Figure 1:
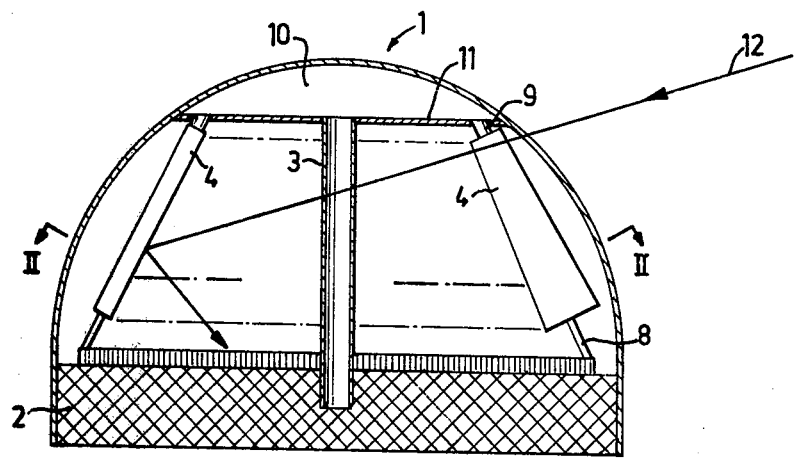

United States Patent [19]

Heden

[11] 4,233,958
[45] Nov. 18, 1980

[54] CLIMATE-CONTROLLED BUILDING CONSTRUCTION

[76] Inventor: Carl-Göran Hedèn, Solna Kyrkväg 11, S-104 01 Stockholm, Sweden

[21] Appl. No.: 922,432

[22] Filed: Jul. 6, 1978

[30] Foreign Application Priority Data

Jul. 7, 1977 [SE] Sweden ............................... 7707943

[51] Int. Cl.³ .............................................. F24J 3/02
[52] U.S. Cl. .................................. 126/424; 126/430; 47/1.4; 47/17
[58] Field of Search ..................... 47/1.4, 17; 237/1 A; 126/270, 428, 424, 430; 49/77, 78, 86; 160/166 A

[56] References Cited

U.S. PATENT DOCUMENTS

| | | | |
|---|---|---|---|
| 2,732,663 | 1/1956 | Dewey | 47/58 |
| 3,182,654 | 5/1965 | Culling | 126/270 |
| 3,450,192 | 6/1969 | Hay | 47/17 X |
| 3,955,317 | 5/1976 | Gudin | 47/1.4 X |
| 4,049,195 | 9/1977 | Rugenstein | 237/1 A |
| 4,054,125 | 10/1977 | Eckels | 126/270 |
| 4,064,648 | 12/1977 | Cary | 47/17 |
| 4,076,013 | 2/1978 | Bette | 126/270 |
| 4,078,332 | 3/1978 | Savins | 47/1.4 |
| 4,095,369 | 6/1978 | Posnansky et al. | 47/17 X |
| 4,108,373 | 8/1978 | Chiapale et al. | 47/17 X |
| 4,114,594 | 9/1978 | Meyer | 126/270 |

FOREIGN PATENT DOCUMENTS

| | | |
|---|---|---|
| 1582871 | 7/1970 | Fed. Rep. of Germany . |
| 2522791 | 12/1975 | Fed. Rep. of Germany . |
| 1555634 | 1/1969 | France . |
| 2304277 | 11/1976 | France .................................. 47/17 |
| 581943 | 11/1976 | Switzerland ............................ 47/17 |
| 1470533 | 4/1977 | United Kingdom ............... 160/166 A |
| 377150 | 9/1973 | U.S.S.R. ................................. 47/1.4 |
| 569810 | 8/1977 | U.S.S.R. ................................ 126/270 |

OTHER PUBLICATIONS

"A Hort-El-Complex in Sweden" Christensen AE-496.

Primary Examiner—Steven A. Bratlie
Attorney, Agent, or Firm—Young & Thompson

[57] ABSTRACT

A building construction formed as a dome has a transparent outer shell and an inner shell of flat cassettes which are turnable for regulating incident light radiation and light escaping from the dome. Air is circulated through a heat accumulator, arranged beneath the dome, and a collecting space in the peak of the dome through the cassettes, which have a shiny and a black side surface for maximum reflection or absorption of sunlight. The adjustment of the cassettes for greatest efficiency is automatically controlled. The dome has double or multiple transparent walls between which biomass is cultivated, e.g. green microorganisms in an outer and red microorganisms in an inner layer for maximum energy utilization. Light-absorbing salt solutions can be circulated through a layer, or parts thereof, when screening-off is desired to steer light radiation for optimum biological production.

1 Claim, 8 Drawing Figures

U.S. Patent    Nov. 18, 1980    Sheet 1 of 2    4,233,958

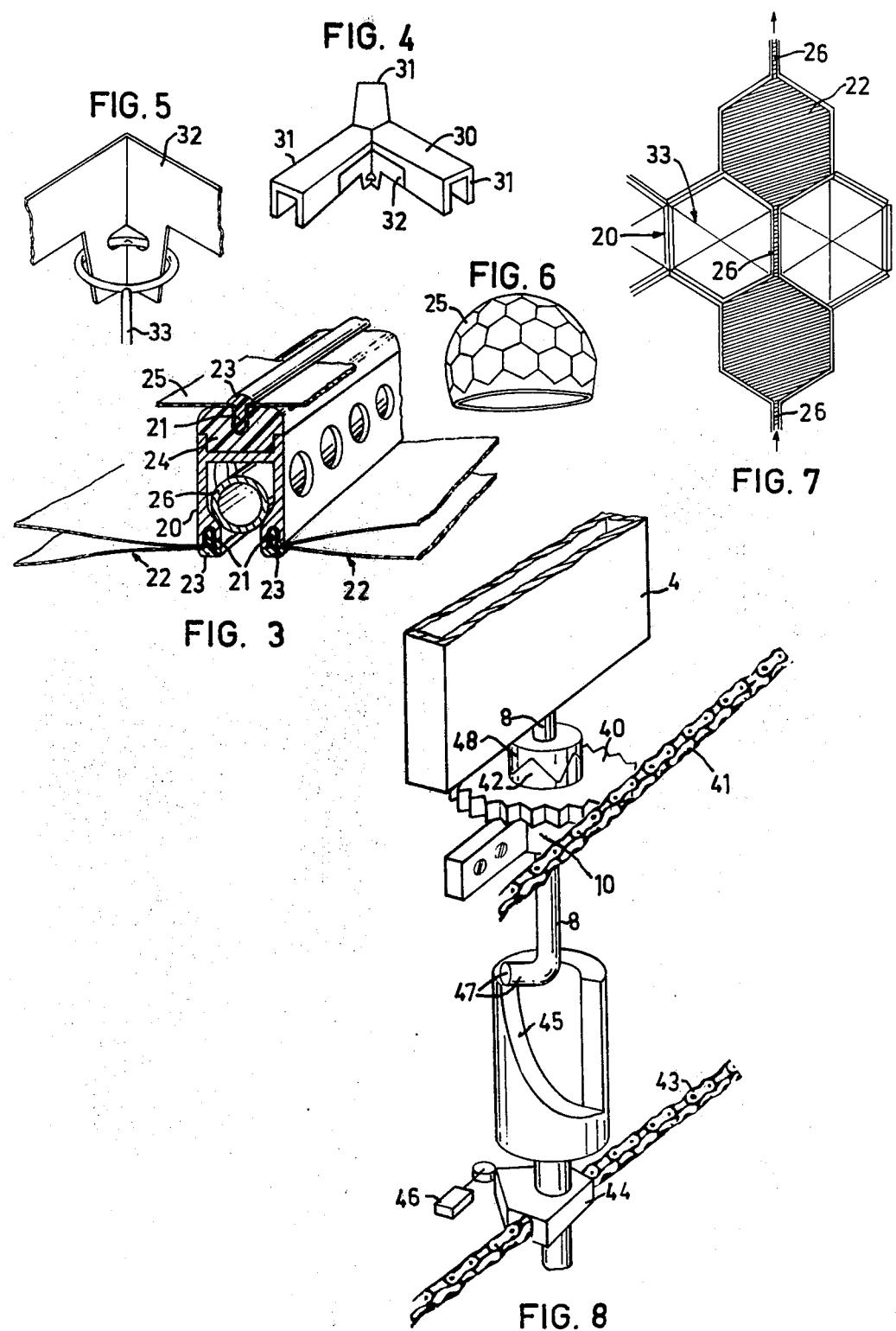

CLIMATE-CONTROLLED BUILDING CONSTRUCTION

Human beings, as well as the plants and animals which make up their food, require temperatures within relatively narrow ranges; temperatures which can only be maintained by storage of solar energy. Thus heating is of great importance for evening-out the frequent changes in light intensity, and fossil fuels, wood and water-power storage balance out the historical and seasonal variations in energy requirements. The tendency of Man to concentrate the consumption of energy both in time (the Industrial Revolution) and in space (urbanisation) has now created problems, thus increasing the interest and attention given to increased self-sufficiency and decentralised energy systems. This has given rise to the development of many more or less autonomous experimental houses. Different components are integrated therein in such a way that the effectiveness of the system is greater than the sum of the individual parts. In the field of architecture, Buckminster Fuller pointed out early on the need for synergistic solutions in the area of mechanics of materials, resulting in a series of simple and elegant geodesic domes.

In my own Swedish Patent Application No. 7510931-4 the possibility is pointed out of using dome constructions to achieve integrated environmental control systems. The present invention is intended to improve and reduce the costs of an environmental control system, aimed at an advanced biosynergetic dome suitable for mass production in kit form or as a component in floating basic module factories according to my Swedish Patent Application No. 7510123-8. The dome is mounted on top of a suitable heat accumulator, a rock storage chamber or an aquiculture pool, possibly in combination with a sedimentation tank which can make methane for producing electricity and for the production of combustible gases, for use in air-lifting and accelerated photosynthesis. However, temperature management will be dealt with only while touching on the production of biomass, for producing feed and methane, for example.

Greenhouse design is, without a doubt, of considerable interest for a country such as Sweden, both as a complement to single-family dwellings and for utilisation of waste heat. See the studies by J. Christensen "A Hort-El-Complex in Sweden", Atomenergi, AE-496, 1974, 82 pages, and "Spillvärme för odling" done for the Swedish Committee for Energy Production Research, 1977. Also of major economic importance are various types of aquiculture as well as thermal horticulture, e.g. asparagus, squash and strawberries, and thermal silvaculture for efficient production of nursery trees. The value of a shell construction will be appreciably increased if it can be used both for the production of biomass and for temperature control of tennis courts and other sport facilities.

The present invention relates to a temperature-controlled dome for plant cultivation, sport facilities etc.

Suitably, the construction is made with two "shells", the outer shell employing a particle suspension or a salt solution as a light absorber and heat transport medium, while the inner shell uses air as a thermal medium. The two shells together create an extremely flexible climate control system, but in many applications only one of the shells will suffice, the outer one, for example, for simple algae cultivation, or the inner one in combination with a simple, pneumatic casing for plant cultivation or aquiculture.

The invention will be described in more detail in connection with an embodiment and the accompanying drawings, showing in FIG. 1, a side cross-sectional view of a dome according to the invention with an underlying heat storage chamber, FIG. 2, a section through FIG. 1 along the line II—II, FIG. 3, a fragmentary perspective view of a beam for constructing the outer shell of the dome, FIG. 4, a connecting piece for the beams, FIG. 5, a locking plate and the fastening of cross stays, FIG. 6, the outer shell of the dome as seen from the outside, FIG. 7, plastic sections for the outer shell of the dome, and FIG. 8, a fragmentary perspective view of a device for climatisation control.

Figure 2:
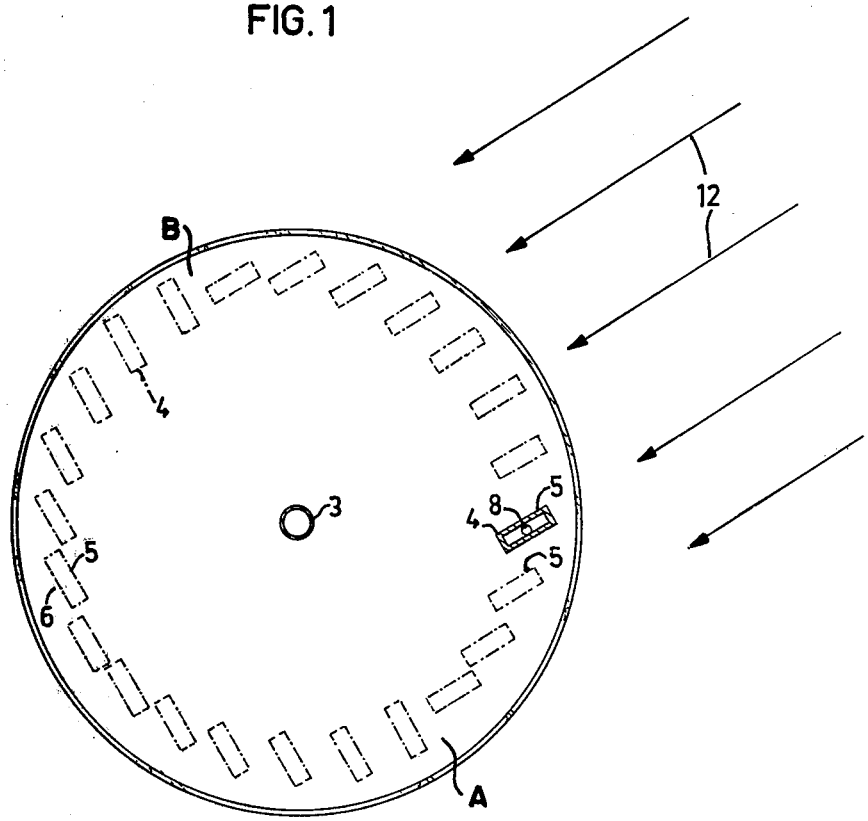

FIG. 1 shows the dome 1 placed on top of a suitable heat accumulator 2, a rock storage chamber for example, whose air content can circulate via a central tubular duct 3 and the interior of the dome through a number of light-absorption cassettes 4. The direction of air flow can be reversed so that during the day, warm air is conducted to the rock storage chamber 2 through the central duct 3, while at night it travels in the opposite direction to be distributed via the cassettes 4 along the periphery of the dome. The cassettes consist of flat, long and narrow boxes, one side surface 5 of which is polished shiny for maximum light reflection, while the other side surface 6 is blackened and structured for maximum light absorption. The ends of the cassettes are provided with journalled axles. The lower axle 8 is solid and the upper axle 9 is tubular to make it possible for the warm air to pass to the connecting space above the dome ceiling. The cassettes are entirely open at their lower ends and closed at their upper ends with the exception of the opening through the tubular axle 9. The cassettes are mounted with their lower axles adjacent to the lower edge of the dome and inclined inwards so that their tubular axles open into the connecting space 10 in the upper portion of the dome. This space 10 is separated from the rest of the dome by a ceiling 11 with openings for the central tube 3 and the tubular axles 9. The cassettes have a tapered shape so that they provide complete coverage when turned to a position parallel with the outer shell.

The cassettes are steered to follow the movement of the sun in such a way that on the side of incidence they are parallel to the direction of the light rays 12, while at the other side of the dome they are perpendicular to the light rays with their shiny surface facing the sun, thus reflecting the light and heat which would otherwise be lost, back into the dome. The control of the angular positions of the cassettes will be described in more detail later.

The outer shell of the dome is constructed of four standard sections, H-shaped aluminum beams, star-shaped connecting pieces, hexagonal plastic sheets and hexagonal plastic containers. FIG. 3 shows an H-shaped aluminum beam 20 with longitudinal grooves 21 in which plastic containers 22 can be fixed with the aid of T-shaped plastic mouldings 23. A strip 24 of teak, plastic or other thermally insulating material is pressed into the outer opening of the aluminum beam 20. This strip has as do the other edges of the aluminum beam, one or more longitudinal grooves 21 into which the outer plastic casing 25 can be fixed with plastic moulding 23 in the same manner as the plastic containers 22. The opening in the beam 20, which faces the interior of the dome, provides a place for connecting hoses 26 between the plastic containers 22.

The construction described above was done with hexagonal plastic sheets and hexagonal plastic containers and with such components it is of course possible to achieve an enormous variety of dome shapes. However, it is also possible to combine different component shapes, for example rows of pentagonal, rectangular or asymmetrical pieces, as a mason inserts halfbricks or the like in a course. It is only of importance to the present invention that the variously shaped containers be adapted to the circulation. An alternative solution is to allow the culture to circulate through a transparent hose laid in close parallel rings on a globe-like framework.

FIG. 4 shows a star-shaped connecting member 30 of an elastic but strong material. The aluminum beams 20 are slipped over the legs 31 of the connecting pieces and over the plates 32 used to anchor and lock the cross stays 33 between the connecting pieces 30. The anchoring plates 32 for the fastening of the cross stays 33 are shown in more detail in FIG. 5. The cross stays 33 serve both to increase the strength of the structure and to support the plastic containers.

The outermost layer of the dome is made up of hexagonal plastic sheets 25 of Mylar ®, Tedlar ® or the like which are anchored in the grooves 21 in the strips 24 on the aluminum beams described above. FIG. 6 shows a dome as seen from the outside. By using this anchoring system, color and other characteristics can be varied between different sections and at different locations on the dome. Thus it is quite conceivable that the area facing the sun's zenith point should be covered with a plastic material which becomes totally reflective when the outer temperature exceeds a certain point. See for example "Exploring Space Conditioning with Variable Membranes" MIT, Cambridge Mass. 1975.

As was mentioned above, the inner layer of the outer shell consists of flat, hexagonal plastic containers 22, and the construction is shown in more detail in FIG. 7. The plastic containers 22 are provided in two opposite corners with the previously mentioned connecting hoses 26 which extend vertically along the dome. Thus the direction of flow in a column of plastic containers is from bottom to top as indicated by the arrows in FIG. 7, and the flow is returned in the adjacent vertical column from top to bottom. The plastic containers contain a suspension or solution which will be described below, and a pump effect in the upward direction is achieved by the introduction of gas bubbles from a pressure line (not shown) at the base of the dome in every other vertical column.

The dome is designed to be able to operate with two alternative media, possibly within different segments of the cupola. In one case the suspension consists of photosynthetically active microorganisms, and in another case of particles which both have good light-absorbitivity and are easily separated from the surrounding liquid in spite of the fact that they preferably have the same specific gravity as said liquid. An example of the first case is Dunaliella algae, which due to its extreme tolerance to salt makes it possible to obviate the problem of contamination.

It is also possible to use double layers of plastic containers, i.e. replace the plastic sheets 25 in the outer layer with plastic containers 22. Cultivation of green microorganisms in the outer plastic containers and red microorganisms in the inner plastic containers utilises a maximum portion of the light spectrum for producing biomass.

An example from the other category would be composite particles with high ferrite content to facilitate magnetic separation, and also containing small glass beads or fat droplets to prevent sedimentation. Each system naturally requires its own specific auxiliary equipment, the first case, for example, requiring means for intermittently flushing the system at high velocity with inert particles to remove any growth on the walls. In the second case magnetic devices are required to keep the particle density at a level corresponding to light screening requirements. For screening out of heat, it is also possible to use a 1 to 2% solution of copper chloride which is capable of filtering out heat but allowing all photosynthetic radiation to pass.

As was mentioned above, there is direct control of the climatisation with the inner shell. All of the cassette axles 8 can be provided with individual gears 40 and the gears can be driven by a common chain 41 which runs around the entire periphery of the dome. By driving the chain 41 with a motor so that the rotational speed for each cassette is exactly one revolution per day, the solar radiation 12 in the dome can always be kept at a maximum by keeping the cassettes on the sun side of the dome parallel with the solar radiation. To prevent the radiation from going out through the back of the dome, the cassettes in the rear half of the dome should be kept perpendicular to the radiation so that it is reflected downwards to the heat collector (see FIG. 1). This can be done by turning the cassettes 90° at two diametrically opposite points A and B. FIG. 8 shows how the gear 40 is provided with a toothed coupling 42, 48 which only permits the cassette 4 to assume two positions which are perpendicular to one another. To achieve the 90° rotation, a bracket 44 for a pusher sleeve 45 is mounted on a chain 43 which moves synchronically with the chain 41. Upon a vertical movement by the pusher sleeve triggered by any conventional mechanism such as a microswitch 46, the angularly curved end 47 of the cassette axle 8 is acted on. The axle is freely movable vertically and is lifted and turned by the pusher sleeve 45 so that a toothed disc 48 on the cassette axle is lifted out of engagement with the toothed disc 42 of the gear 40 and is also turned by the pusher sleeve 90° and then returns into engagement with the toothed disc of the gear.

A corresponding pneumatic or hydraulic driving and guiding of the movement of the cassettes is also quite possible, as is the triggering of the movements from a central unit to which temperature control can also be connected.

By virtue of the fact that the cassettes are blackened on one side and shiny on the other, the degree of reflection or absorption can be easily regulated by giving the chains a corresponding displacement forwards or backwards thus changing the positioning of all of the cassettes in relation to the solar radiation. It is possible to seal the dome with the shiny sides of the cassettes inwards and thus reduce the artificial supplementary illumination required for controlling blooming cycles or the like.

An interesting application of the present invention has proven to be the arrangement of the domes on an annular raft, for example. In this way climatisation control can be effected by turning the entire raft and thus eliminating a number of the parts required in stationary, land-based domes. This is a very interesting possibility especially for algae cultivation, since circulation can be achieved through the normal wave movement, or possibly by using wave energy to produce both pumping energy and energy for circulation of the algae culture itself. External constructions can have many forms, for example a net cage under the raft for raising fish, which would feed the algae, and a device for harvesting the algae in a black harvesting funnel, with a light-colored disc in the bottom. The flagellae-carrying sea algae themselves would swim to and collect in the light, narrow portion of the funnel.

What I claim is:

1. Device for carrying out climate control in a building, comprising a heat storage chamber (2), a dome (1) built on top of it with a transparent outer shell (25, 22) and an inner shell composed of flat cassettes (4) rotatably arranged to be able to screen off incident light radiation to a greater or lesser degree in the dome (1) and the escape of light therefrom, there being for heat exchange between the heat storage chamber (2) and the dome (1) a central tube (3) from the heat storage chamber (2) to an upper connecting space (10) in the top of the dome, a hollow, upper axle (9) on each cassette (4) opening into the connecting space (10) and a lower, open end surface on each cassette (4) opening into the dome, the outer shell being made up of an outer layer (25) and an inner layer (22), at least the inner layer being composed of flat plastic containers (22) arranged with an upper and a lower corner, said corners having openings for connection to connecting hoses (26) and adjacent columns of plastic containers (22) being pairwise connected together with connecting hoses (26) to closed circulation loops, said dome (1) being made up of a frame of aluminum beams (20) and strips (24) having grooves (21) in which the plastic containers (22) and the plastic sheets (25) are clamped with plastic moldings (23), said aluminum beams (20) being held together with star-shaped connecting members (30) to form an approximately hemispherical dome frame with a honeycomb structure, said cassettes (4) having a shiny, reflecting side surface (5) and a black, heat-absorbing side surface (6) and being mounted substantially vertically and being rotatable on two axles (8, 9) of which at least the upper axle (9) is hollow and connects the interior of the cassette to the connecting space (10), while the bottom of the cassette is open and in free communication with the dome, a gear (40) controlling the setting of the cassettes on the lower axle (8) of the cassette, a chain (41) running over and in engagement with the gears (40) of all the cassettes and a motor for driving the chain (41) synchronically with the movement of the sun, a magnetic device to move a guide cylinder (45) vertically, a pin (47) on the lower axle (8) of the cassette, which pin can be acted on by the guide cylinder (45), a toothed coupling (42, 48) between the cassette axle (8) and the gear (40) to fix different positions with 90° between them between the gear and the cassette axle when the guide cylinder (45) acts on the axle pin (47), and a chain (43) for triggering the action of the guide cylinder (45), the last-named said chain (45) moving synchronically with the first-named said chain (41).

* * * * *